(12) United States Patent
Pitzen et al.

(10) Patent No.: US 6,834,206 B1
(45) Date of Patent: Dec. 21, 2004

(54) METHOD FOR THE ELECTRICAL STIMULATION OF HUMAN TISSUE TO ENCOURAGE HAIR GROWTH

(75) Inventors: Sylvester A. Pitzen, Phoenix, AZ (US); Elizabeth Pitzen, Phoenix, AZ (US)

(73) Assignee: Sono-Therapy Institute, Inc., Phoenix, AZ (US)

( * ) Notice: Subject to any disclaimer, the term of this patent is extended or adjusted under 35 U.S.C. 154(b) by 0 days.

(21) Appl. No.: 10/744,187

(22) Filed: Dec. 23, 2003

(51) Int. Cl.⁷ .............................................. A61N 1/18
(52) U.S. Cl. ............................ 607/50; 607/68; 607/70; 607/145; 601/15
(58) Field of Search ............................ 607/50, 68–72, 607/76, 145; 601/15

(56) References Cited

U.S. PATENT DOCUMENTS

| | | | |
|---|---|---|---|
| 3,872,859 A | | 3/1975 | Pitzen et al. ............... 601/15 |
| 4,751,927 A | * | 6/1988 | Yamada ...................... 606/187 |
| 5,484,387 A | | 1/1996 | Pitzen .......................... 601/15 |
| 5,800,477 A | * | 9/1998 | Groux ......................... 607/76 |
| 6,332,097 B1 | | 12/2001 | Beder ......................... 607/139 |
| D478,994 S | | 8/2003 | Pitzen ........................ D24/200 |
| 6,620,158 B2 | * | 9/2003 | Ronci .......................... 606/36 |

OTHER PUBLICATIONS

Gunn & Lee, Male–Pattern Hair Loss—A Supraorbital Nerve Entrapment Syndrome? Acupuncture & Electro–Therapeut. Res., Int., vol. 5, pp. 83–91, 1980.

* cited by examiner

*Primary Examiner*—Carl H. Layno
(74) *Attorney, Agent, or Firm*—Jordan M. Meschkow; Lowell W. Gresham; Meschkow & Gresham, P.L.C.

(57) ABSTRACT

A method for applying a therapeutic signal (24) to a body portion (34) of a subject (20) to encourage hair growth utilizes an apparatus (22) that includes a first electrode (28) and a second electrode (32). The first electrode (28) is secured in contact with the skin surface of the subject (20) remote from the body portion (34), and the second electrode (32) is positioned at the body portion (34). The therapeutic signal (24) is provided at a conductive pod (114) of the second electrode (32). The second electrode (32) is manipulated by an operator to apply a circular motion (134) to the body portion (34) underlying the conductive pod (114). The circular motion (134) is repetitively applied as the conductive pod (114) is moved across the body portion (34) to loosen connective tissue at the body portion (34).

15 Claims, 5 Drawing Sheets

METHOD FOR THE ELECTRICAL STIMULATION OF HUMAN TISSUE TO ENCOURAGE HAIR GROWTH

RELATED INVENTION

The present invention is related to "Apparatus For the Electrical Stimulation of Human Tissue," by Sylvester A. Pitzen et al., U.S. patent application Ser. No. 10/295,680, filed 15 Nov. 2002, which is incorporated by reference herein.

RELATED PATENT

The present invention is related to "Electrode For Stimulating The Skin," by Sylvester A. Pitzen, U.S. Pat. No. D478,994, issued 26 Aug. 2003, which is incorporated by reference herein.

TECHNICAL FIELD OF THE INVENTION

The present invention relates to the field of electrical stimulation of human tissue. More specifically, the present invention relates to a method for applying a therapeutic signal to human tissue to aid in loosening connective tissue and stimulating blood circulation to encourage hair growth.

BACKGROUND OF THE INVENTION

In an age of great emphasis on youth and beauty, hair loss has become a major concern. Indeed, some sort of baldness (alopecia) affects a significant percentage of the total male population. Some women also experience thinning of the hair as they age, although baldness in women is rare. Male pattern baldness is the most common form of baldness, and begins with hair loss from the vertex and the frontoparietal regions of the scalp, ultimately leaving only a sparse peripheral rim of scalp hair. A hair follicle is a tube-like opening into the epidermis where a hair develops, and a hair root is the part of a hair that is embedded in the hair follicle. In affected areas, the hair follicles produce finer and lighter terminal hairs until terminal hair production ceases.

The cause of male pattern baldness is unknown. However, it is theorized that male pattern baldness may be caused by a combination of factors that include, for example, the vascular composition of the individual, the physical structure of an individual's scalp, aging, and the male characteristic hormone, testosterone. In other words, poor blood circulation in the scalp, non-elasticity of the scalp tissue resulting from increased cross-linkage of connective tissue, loss of skin elasticity due to aging, and testosterone play a role in male pattern baldness. This combination of factors is believed to cause a deprivation of the trophic, or nutritional factor, of hair follicles. This deprivation of adequate nutrition results in shortening of the hair follicles and eventual cessation of hair production. When the hair follicles have been destroyed, alopecia is thought to be irrevocable. However, in the early stages before total follicular damage, restoration of the nutritional factor is thought to help.

In response to the distress of those suffering from male pattern baldness, a multitude of treatments have been devised in an attempt to stop and/or reverse the process of hair loss. These treatments include medications, hair transplants, scalp exercise, low voltage electrical stimulation, and so forth. Although many have claimed to have solved the problem, in whole or in part, there has yet to be found a definitive solution that will truly mitigate the problem of undesired hair loss.

One technique that has met with limited success is the application of low voltage electrical stimulation to the skin layers of the scalp through an electrode coupled with massage. A device is utilized that generates numerous square wave voltage waveforms, each of a different frequency. These are turned on and off at various intervals, to yield a continuously varying signal. The combined use of low voltage electrical stimulation and massage is believed to loosen the skin layers and connective tissue in the scalp. The treatment has resulted in the retardation of hair loss for some, and has resulted in the rejuvenation of hair growth in others.

Low voltage electrical stimulation has had limited success, due in part because of non-optimal signal characteristics produced by prior art devices, inadequate surface contact between the electrode and the body portion undergoing treatment, and ambiguous perceived "operator feel." By way of example, it is believed that in one prior art device, the rise time and fall time of the generated square waves utilized to produce the therapeutic signals is undesirably slow. This results in a less than optimum therapeutic signal and less effective treatment.

The administration of the treatment is enhanced by a perceived "operator feel." That is, an operator must be trained to experience a physical sense of increased resistance to the massaging action in the region of taut skin and dense connective tissue, i.e., the "tight regions." When stimulated by electricity, this physical sense of increased resistance is enhanced. It is theorized that the effectiveness of the treatment can be speeded up by focusing treatment on these tight regions. A prior electrode utilized for treatment has a flattened tip, and an operator is compelled to hold the electrode substantially perpendicular relative to the body portion being treated. This electrode shape makes it difficult for the operator to apply the appropriate pressure and massage technique to the body portion being treated, while concurrently sensing through "operator feel" this increased resistance to the massaging action in tight regions in response to the treatment. The inadequate surface contact between the electrode and the body portion undergoing treatment, and ambiguous perceived "operator feel" due to the position in which the electrode is held results in undesirably lengthy operator training and/or less effective, treatments.

As such, it is highly desirable to improve the success rate of the aforementioned electrical stimulation technique for the encouragement of hair growth.

Stress, brought about by lifestyle, chronic pain, and/or other health issues, may play an important part in hair loss. During periods of high stress, it has been noted that some individuals suffer from increased shedding of the hair and/or a decrease in new hair production. If there is increased shedding and decreased new production of hair, there will be less visible hair on the scalp. Accordingly hair loss may be exacerbated for those individuals in stressful situations. Consequently, it is desirable to incorporate a stress reduction methodology into the electrical stimulation technique for the further encouragement of hair growth.

SUMMARY OF THE INVENTION

Accordingly, it is an advantage of the present invention that a method is provided for applying a therapeutic signal to a body portion to encourage hair growth.

It is another advantage of the present invention that a method is provided that employs an electrical stimulation technique and a massaging motion that loosens connective tissue thereby improving the nutritional factor of the subject body portion.

Another advantage of the present invention is that method is performed on successive body portions to achieve subject relaxation, pain relief, and commensurate stress reduction.

The above and other advantages of the present invention are carried out in one form by a method of applying a therapeutic signal to a body portion of a subject to encourage hair growth. The method calls for securing a first electrode in contact with a skin surface of the subject remote from the body portion, the first electrode being maintained at a ground potential from which the therapeutic signal is referred. The method further calls for positioning a second electrode at the body portion, the second electrode including a conductive pod and a grip interconnected with the conductive pod, and providing the therapeutic signal at the second electrode. The second electrode is manipulated by an operator at the body portion. The operator utilizes both hands to manipulate the second electrode such that a first one of the hands applies pressure to the conductive pod, a second one of the hands applies force on the grip, and the hands act cooperatively to apply a circular motion to the body portion underlying the conductive pod. The circular motion is repetitively applied as the conductive pod is moved across the body portion to loosen connective tissue at the body portion.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

The primary focus of the present invention is directed to the enhancement of conditions favorable for the encouragement of hair growth. In particular, the present invention serves to loosen connective tissue and improve blood circulation in the scalp. In addition, the present invention serves to achieve subject relaxation, pain relief, and commensurate stress reduction for the subject. However, the loosening of connective tissue, improved blood circulation, and subject relaxation have benefits for other physical impairments as well. Injuries or disease affecting body tissue may similarly reduce elasticity of tissue and create blood circulation problems. As such, the treatment method discussed herein may alternatively be applied to other areas of the body to improve the condition of connective tissue and blood circulation.

Figure 1:
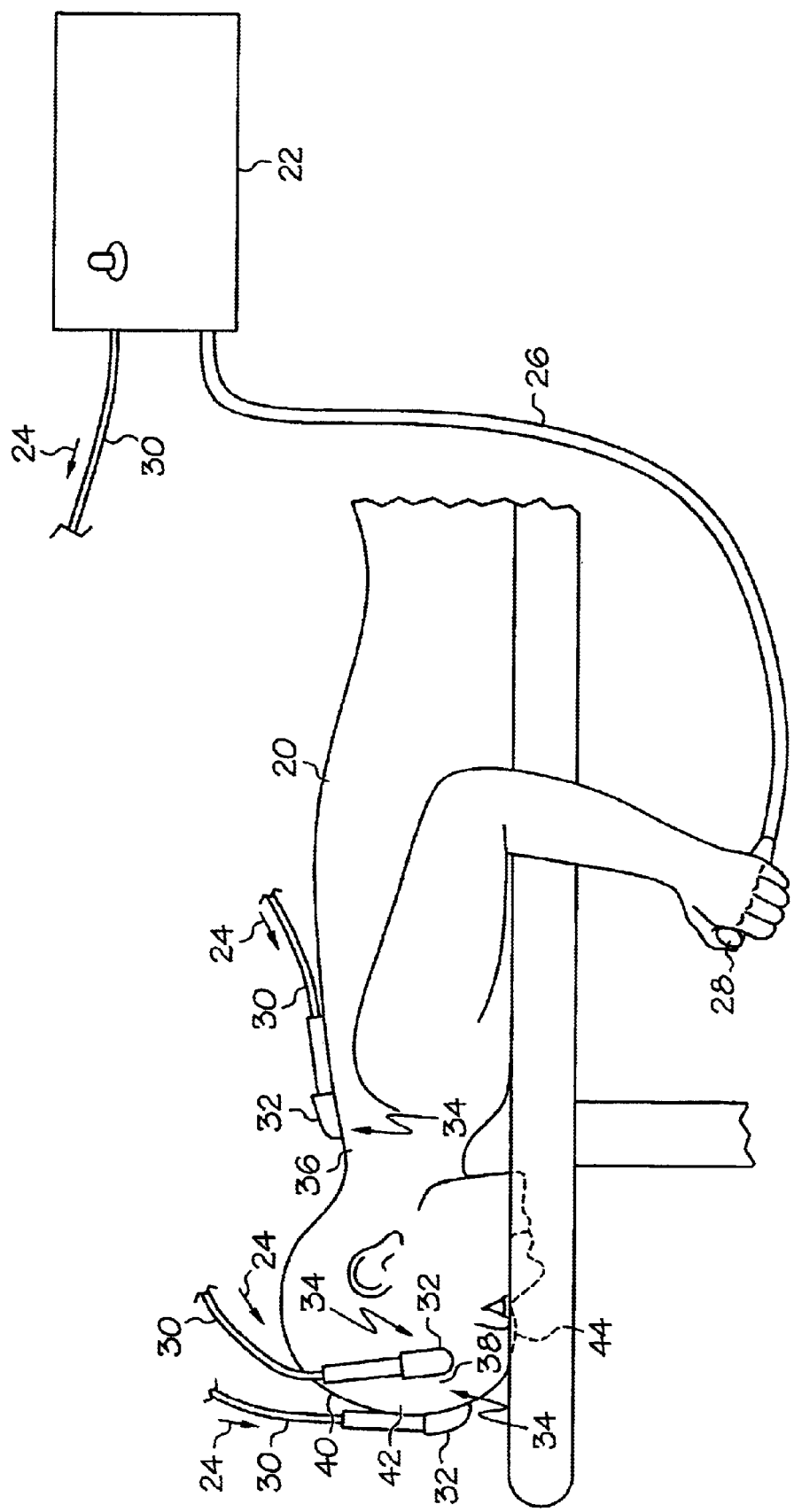
FIG. 1 shows a side view of a subject lying face down upon whom a method in accordance with the present invention may be performed.
Figure 2:
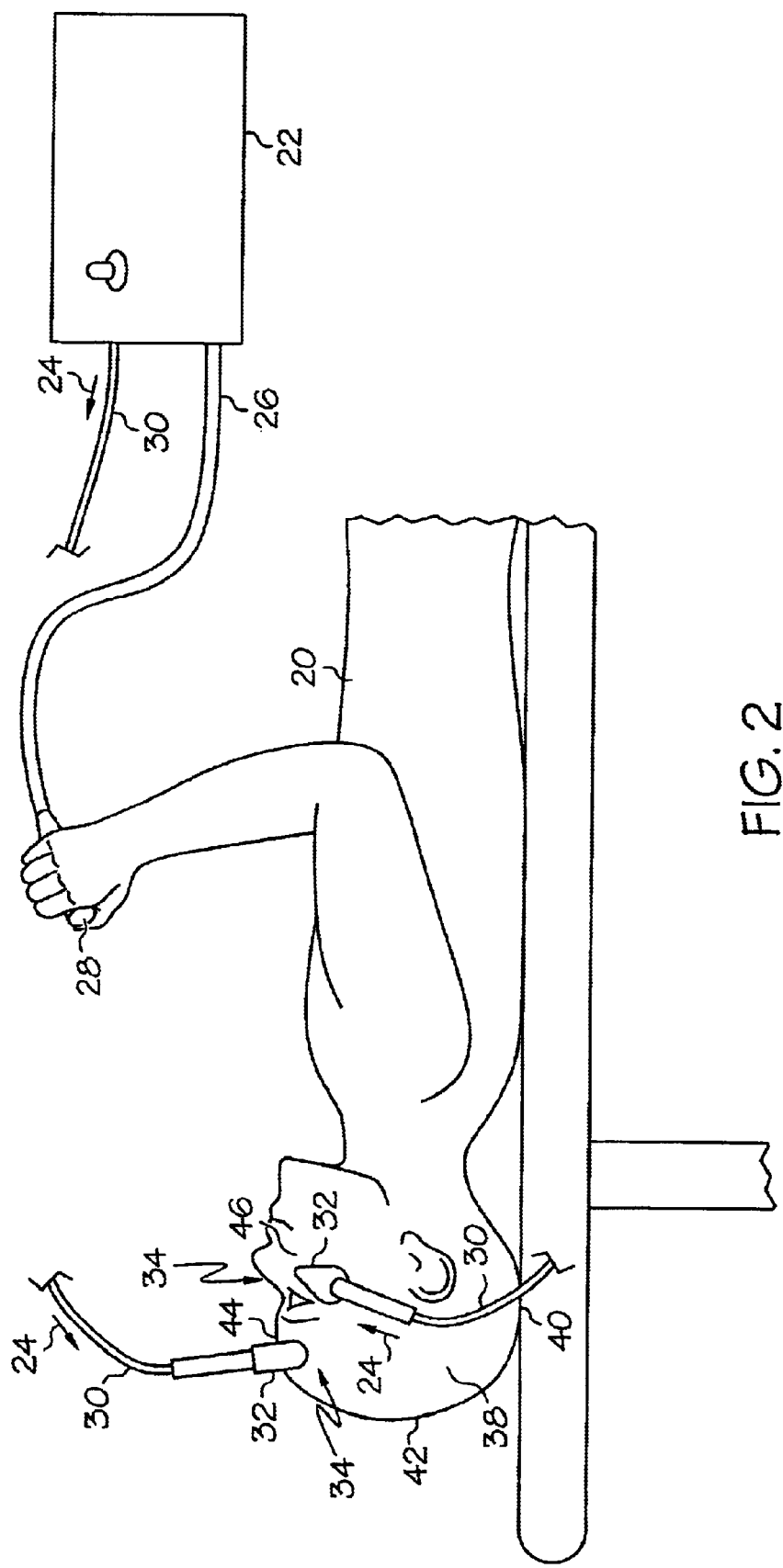
FIG. 2 shows a side view of a subject lying face up upon whom the method in accordance with the present invention may be performed.

Referring to FIGS. 1–2, FIG. 1 shows a side view of a subject 20 lying face down upon whom a method in accordance with the present invention may be performed. FIG. 2 shows a side view of subject 20 lying face up upon whom the method in accordance with the present invention may be performed. Subject 20 may be laying on a massage table having a conventional headrest that comfortably cradles the subject's face when subject 20 is in the face down position. As such, the subject's face is shown partially in ghost form in FIG. 1 when cradled in the headrest.

The present invention is an improved low voltage electrical stimulation technique utilizing an apparatus 22 for provision of a therapeutic signal, represented by an arrow 24. Apparatus 22 includes a first conductor 26 terminating at a first electrode 28 and a second conductor 30 terminating at a second electrode 32. First electrode 28 is maintained at a ground potential from which therapeutic signal 24 from second electrode 32 is referred.

Each of first and second electrodes 28 and 32 are fabricated from highly conductive material, such as, fine silver, which is at least ninety-nine percent pure silver, or gold plating. The highly conductive material enables low resistance between the electrode and subject. First electrode 28 is gripped by subject 20 to secure first electrode 28 in contact with the subject's palm, and second electrode 32 is in contact with a body portion 34 of subject 20. Therapeutic signal 24 passes between first and second electrodes 28 and 32, respectively, via body portion 34, through the body of subject 20.

In connection with the use of apparatus 22 to loosen connective tissue and improve blood circulation, as well as to achieve subject relaxation, pain relief, and commensurate stress reduction for the purpose of encouraging hair growth, body portion 34 is selected from a group consisting of the subject's shoulders 36, sides 38 of the subject's head 40, top 42 of head 40, forehead 44, and surrounding the subject's eyes 46. More particularly, the methodology described below is successively performed at each of shoulders 36, and sides 38 followed by top 42 of head 40. The methodology continues with forehead 44 and finishes with the face and region surrounding the subject's eyes 46.

Figure 3:
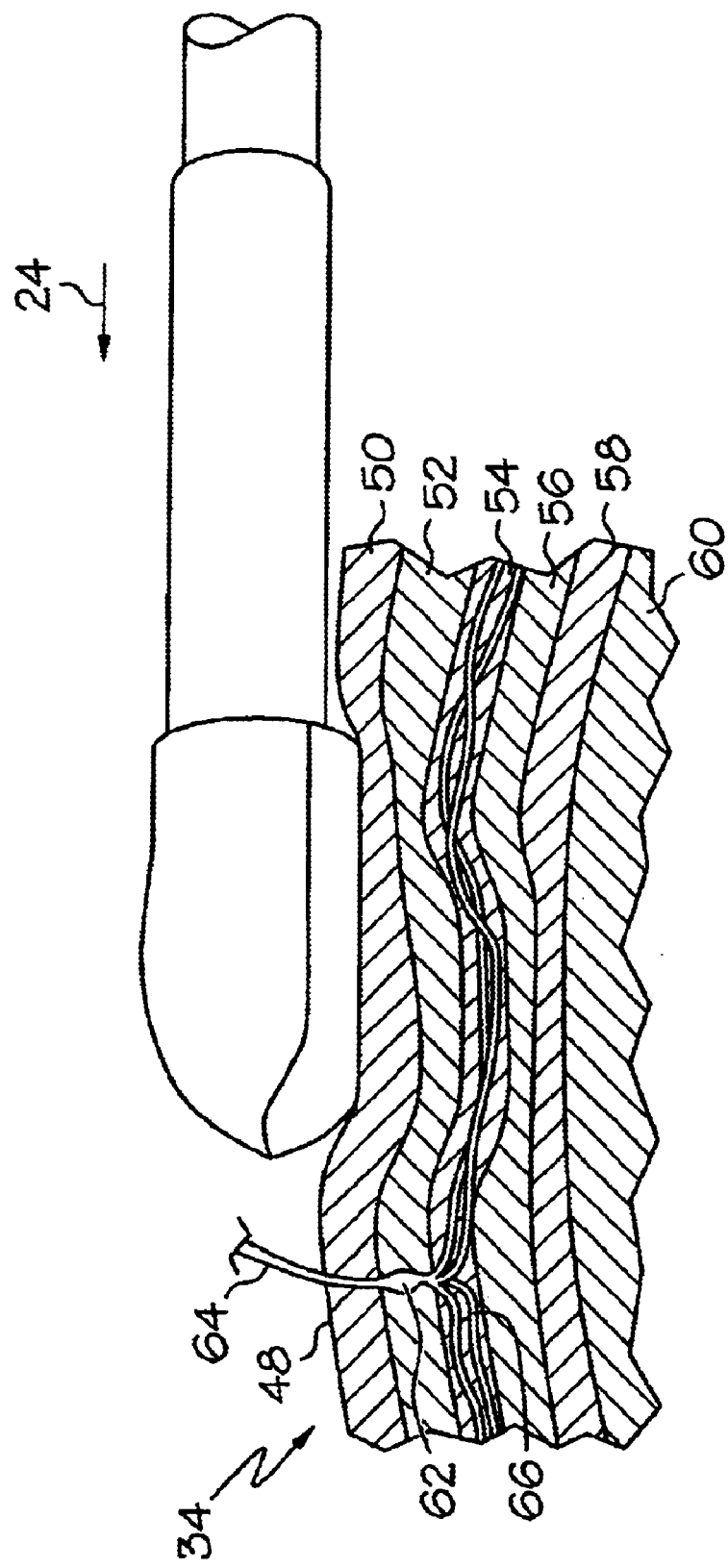
FIG. 3 shows an enlarged cross-section view of the scalp of the subject of FIG. 1 upon which treatment is being applied.

FIG. 3 shows an enlarged cross-section view of body portion 34 of the subject of FIG. 1 upon which treatment is being applied. In particular, treatment is being applied on top 42 (FIG. 2) of head 40 (FIG. 2), i.e., the subject's scalp 48. In general, scalp 48 includes the epidermis 50, the dermis 52, the adipose tissue layer 54, and the epicranial aponeurosis, or galea 56. Galea 56 is a thin tendinous sheet, tightly attached to dermis 52 and is moveable anteriorly and posteriorly. Loose areolar connective tissue 58 loosely connects galea 56 to the periosteum of the skull bone 60. Connective tissue 58 is an irregularly arranged connective tissue that is generally made up largely of interlacing fibers. Skull bone 60 forms a rigid base upon which scalp 48 rests. Hair follicles 62, of which one is shown, are embedded in scalp 48. A hair 64 extends from hair follicle 62 above scalp 48. Blood vessels 66 provide oxygenation and nourishment to the hair root and hair follicle 62.

When scalp 48 moves freely upon skull 60, scalp 48 is considered herein to be "loose", and the organs within scalp 48 are free to function properly. It is believed that the aging process causes a thickening and tightening of the skin layers, particularly in the underlying galea 56 and connective tissue 58. When galea 56 is greatly thickened and tightened, scalp 48 cannot move freely upon skull 60. Thus, scalp 48 is considered herein to be "tight", and the organs within scalp 48 are prohibited from normal functioning. More specifically, the aging process tends to restrict blood flow through blood vessels 66, which in turn causes a shrinking of hair follicles 62. The shrinking or shortening of hair follicles 62 causes a withdrawal of the hair root and hair follicles 62 from blood vessels 66 to impede nourishment of the hair roots and hair follicles 62. The gradual growth dormancy results in hair loss. Since galea 56 does not thicken and harden consistently throughout its area, a given scalp 48 may have both tight spots and loose spots.

Therapeutic signal 24, produced by apparatus 22 is a low voltage electrical variable impulse signal in the range of, for example −0.250 volt and 1.350 volt. Therapeutic signal 24 has an electrical potential sufficient to stimulate scalp 48. Therapeutic signal 24 penetrates through scalp 48 and particularly through galea 56 and connective tissue 58. Simultaneously, particularly where the operator is able to detect tightness of skin, the total skin thickness, i.e., all the skin layers, is "worked" to loosen the layers. Repeated massage and electrical stimulation acts as nerve stimulation which facilitates a "reawakening" or reversal of the natural nourishment processes in scalp 48, which have gradually ceased to function properly on their own.

Figure 4:
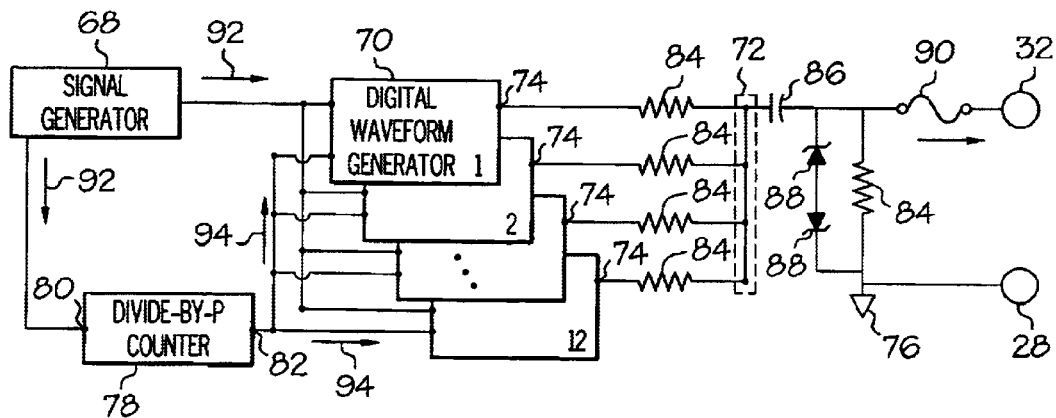
FIG. 4 shows a block diagram of an apparatus utilized with the method of the present invention.

FIG. 4 shows a block diagram of apparatus 22 utilized with the method of the present invention. Apparatus 22 includes a signal generator 68 and a plurality of digital waveform generators 70 in communication with signal generator 68. A combiner, generally denoted by dashed lines 72, is in communication with an output 74 of each of waveform generators 70. Second electrode 32 is in electrical communication with combiner 72, and first electrode 28 is maintained at a ground potential 76.

Apparatus 22 further includes a divide-by-P counter 78. Divide-by-P counter 78 has a divider input 80 in communication with signal generator 68 and a divider output 82 in communication with each of digital waveform generators 70. Resistors 84, a capacitor 86, diodes 88, and a fuse 90 are configured in accordance with conventional electrical circuit practices for providing signal isolation and safety mechanisms.

In operation, signal generator 68 provides a first reference signal, represented by an arrow 92, to each of digital waveform generators 70 and to divide-by-P counter 78. In an exemplary embodiment, first reference signal 92 may be a 15 MHz clock signal that is input into each of digital waveform generators 70, and into divide-by-P counter 78. Each of digital waveform generators 70 is configured to produce a resultant signal related to first reference signal 92, discussed below.

Divide-by-P counter 78 is a frequency divider that produces a second reference signal, represented by an arrow 94, related to first reference signal 92. In an exemplary embodiment, divide-by-P counter 78 is configured such that "P" is five thousand. Accordingly, when first reference signal 92 is 15 MHz, divide-by-P counter 78 produces second reference signal 94 of 3 kHz. Second reference signal 94 of 3 kHz is subsequently provided to each of digital waveform generators 70, as will be discussed in greater detail below. In general, the resultant signal produced by each of digital waveform generators 70 is also related to second reference signal 94, discussed below.

Figure 5:
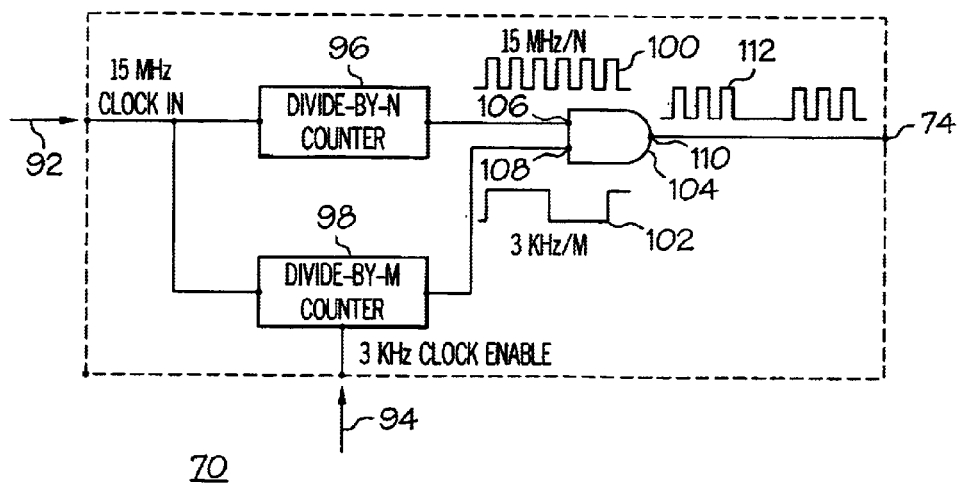
FIG. 5 shows a block diagram of a digital waveform generator of the apparatus of FIG. 4.

FIG. 5 shows a block diagram of one of digital waveform generators 70 of apparatus 22 (FIG. 4). Digital waveform generator 70 includes a divide-by-N counter 96 and a divide-by-M counter 98. Each of counters 96 and 98 is configured to receive first reference signal 92. Divide-by-M counter 98 is further configured to receive second reference signal 94. First reference signal 92 received by divide-by-M counter 98 serves as a synchronization signal to synchronize the operation of divide-by-M counter 98 with divide-by-N counter 96.

Divide-by-N counter 96 is a first frequency divider that divides an input frequency, i.e., 15 MHz first reference signal 92 by a value "N". The output signal, i.e., a first resultant signal portion 100, of divide-by-N counter 96 is a one clock-cycle wide square wave, which occurs at a rate equal to the 15 MHz first reference signal 92 divided by N. Similarly, divide-by-M counter 98 is a second frequency divider that divides an input frequency, i.e., 3 kHz second reference signal 94 by a value "M". The output signal, i.e., a second resultant signal portion 102, of divide-by-M counter 98 is a one clock-cycle wide square wave, which occurs at a rate equal to the 3 kHz second reference signal 94 divided by M.

A logic gate 104 is in electrical communication with an output of each of divide-by-N and divide-by-M counters 96 and 98, respectively. Logic gate 104 has a first gate input 106 for receiving first resultant signal portion 100 and a second gate input 108 for receiving second resultant signal portion 102. In addition, logic gate 104 has a gate output 110 for producing a resultant signal 112.

In an exemplary embodiment, logic gate 104 is an AND gate. An AND gate simulates the function of the logical operator AND. As such, AND gate 104 emits resultant signal 112 only when first and second resultant signal portions 100 and 102, respectively, are coincident, i.e., only when portions 100 and 102 are "high". Furthermore, since divide-by-M counter 98 is synchronized with divide-by-N counter 96, resultant signal 112 is a square wave signal with sharp rising and falling edges. Each resultant signal 112 from each of digital waveform generators 70 is subsequently combined at combiner 72 (FIG. 4) to produce therapeutic signal 24 at second electrode 32.

In a preferred embodiment, the value "IN" for divide-by-N counter 96 and the value "M" for divide-by-M counter 98 are advantageously selected such that resultant signals 112 from digital waveform generators 70 are harmonically non-related. Accordingly, the generated therapeutic signal 24 has a pseudorandom signal characteristic. It is believed that the pseudorandom signal characteristic of therapeutic signal 24 is most effective for stimulating human tissue, such as scalp 48 (FIG. 3).

Figure 6:
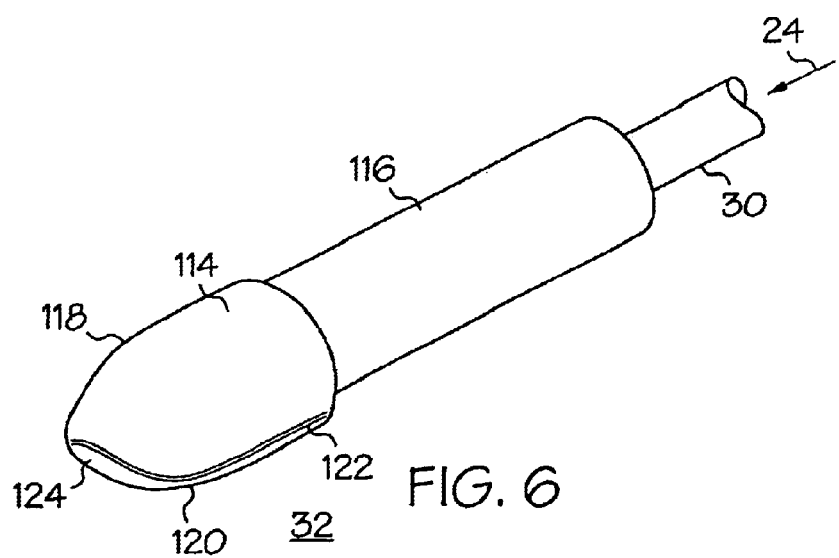
FIG. 6 shows a perspective view of an electrode for stimulating a body portion utilized in connection with the method of FIGS. 1–2.
Figure 7:
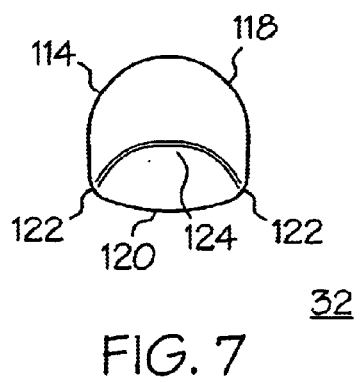
FIG. 7 shows a top view of the electrode of FIG. 6.

Referring to FIGS. 6–7, FIG. 6 shows a perspective view of second electrode 32 for stimulating body portion 34 (FIG. 1) utilized in connection with the method of FIGS. 1–2, and FIG. 7 shows a top view of second electrode 32. Second electrode 32 includes a conductive pod 114 and a non-conductive grip 116 coupled to said conductive pod 114. Conductive pod 114 is electrically connected to second conductor 30 so that therapeutic signal 24 is conveyed to conductive pod 114. Conductive pod 114 has an arcuate side 118 and a generally flat side 120. Arcuate side 118 and flat side 120 are coupled along corresponding longitudinal edges 122 and merge at an end to form an electrode tip 124.

The varying shape of second electrode 32 advantageously enables the operator to selectively utilize any of arcuate side 118, flat side 120, longitudinal edges 122, and electrode tip 124 in response to a particular body portion 34 (FIG. 1) being treated. That is, a particular region of second electrode 32 may be utilized to maximize the effectiveness of the treatment. For example, it has been found that arcuate side 118 and longitudinal edges 122 are effectively used to treat shoulders 36 (FIG. 1), sides 38 (FIG. 1) and top 42 (FIG. 1) of head 40 (FIG. 1), and forehead 44 (FIG. 2). Flat side 120 and electrode tip 124 are effectively used to treat the area surrounding eyes 46 (FIG. 2). In particular, second electrode 32 is tilted roughly forty-five degrees relative to the treatment surface surrounding eyes 46 so that a combination of flat side 120 and electrode tip 124 are used. It has also been found that the soft tissues of the face, such as, the cheeks, lower jaw region, and the throat, may achieve benefit of treatment utilizing flat side 120 of conductive pod 114.

Figure 8:
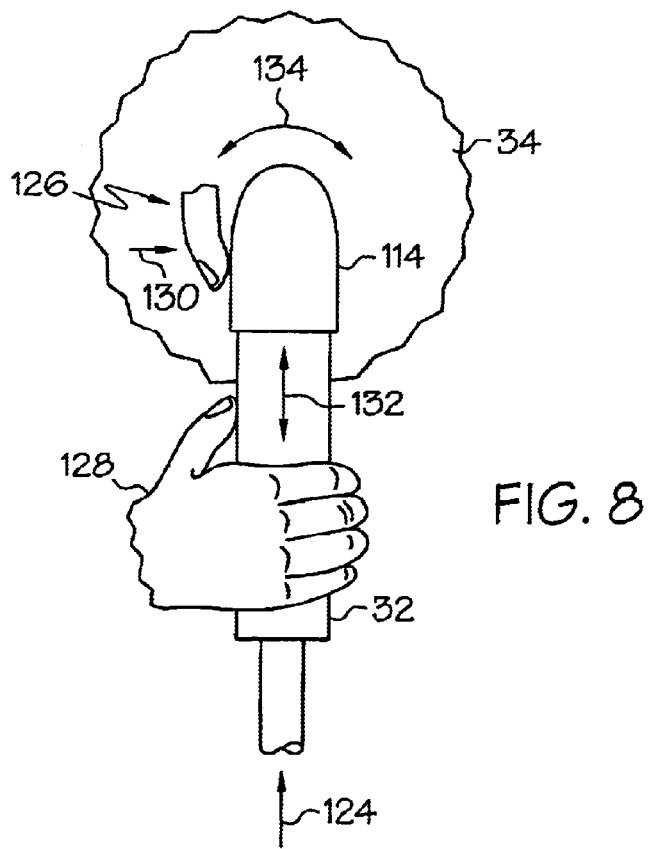
FIG. 8 shows an enlarged front view of the electrode of FIG. 6 in use on the scalp of the subject of FIG. 1 to perform the method in accordance with a preferred embodiment of the present invention.

FIG. 8 shows an enlarged front view of second electrode 32 in use on body portion 34 of subject 20 (FIG. 1) to perform the method in accordance with a preferred embodiment of the present invention. That is, the preferred treatment methodology is thus described in connection with FIG. 8. Body portion 34 and the method of applying therapeutic signal 24 to body portion 34 is described in general terms below for clarity of discussion. However, the method described below is successively performed at each of shoulders 36, sides 38 and top 42 of head 40, forehead 44, and surrounding eyes 46 to accomplish a total treatment regime.

The method of applying therapeutic signal 24 to body portion 34 begins with subject and electrode positioning. In particular, subject 20 is placed in either a face down, face up, or onside position in accordance with subject comfort and operator preference. First electrode 28 (FIG. 1) is secured in contact with a skin surface of subject 20 remote from body portion 34. In a preferred scenario, subject 20 is asked to grasp a conductive portion of first electrode 28.

Next, second electrode 32 is positioned at body portion 34 to be treated so that conductive pod 114 contacts body portion 34. Therapeutic signal 24 is provided at second electrode 32. Apparatus 22 (FIG. 1) may be activated, i.e., turned on, once second electrode 32 is positioned at body portion 34. Alternatively, apparatus 22 may have been activated prior to positioning second electrode 32 at body portion 34.

Once positioned, second electrode 32 is manipulated by an operator who is generally represented by a left hand 126 and a right hand 128 in FIG. 8. The operator utilizes both hands to manipulate second electrode 32 and to detect the tight regions. In this instance, the operator utilizes his or her left hand 126 to apply pressure, represented by an arrow 130, to conductive pod 114. In particular, the thumb of the left hand 126 is laid against conductive pod 114 to apply pressure 130 to conductive pod 114 and to control movement of conductive pod 114. In addition, the operator holds grip 116 in his or her right hand 128 and applies forward and backward force, represented by an arrow 132, on grip 116, and consequently, conductive pod 114. Left and right hands 126 and 128 act cooperatively to effect a circular motion, represented by a curved arrow 134, to body portion 34 underlying conductive pod 114.

Circular motion 134 is repetitively applied as conductive pod 114 is moved across body portion 34. That is force 132 applied by right hand 128 causes conductive pod 114 to "creep", or gradually shift position, across body portion 34. The application of therapeutic signal 24 combined with the circular motion 134 and creeping of conductive pod 114 across body portion 34 serves to loosen connective tissue and improve blood circulation, as well as to achieve subject relaxation, pain relief, and commensurate stress reduction for the purpose of encouraging hair growth.

In addition, the close presence of left hand 126 at body portion 34 enables an operator to feel the physical sense of increased resistance to therapeutic signal 24 and to the manipulating action in the region of taut skin and dense connective tissue, i.e., the "tight regions." Accordingly, the operator can readily focus the treatment on these tight regions thereby enhancing the effectiveness of the treatment.

EXAMPLE 1

Subject A has participated in the aforementioned treatment methodology. Prior to treatment, subject A complained of chronic pain in the left scapula region and suffered from hair loss at the vertex and the frontoparietal regions of the scalp. Through the treatment, subject A reported relief from pain. Specifically, with early treatments, subject A reported cessation of pain in the left scapula region for a period of several days. After several days, the pain returned, but was less uncomfortable. Following approximately four weeks of treatment, the periods of complete pain cessation had reportedly lengthened, while the periods with some discomfort were getting shorter. Subject A now reports complete cessation of pain. In addition, subject A noted that the top of his head appears darker due to new growth of hair in the balding areas.

EXAMPLE 2

Subject B has participated in the aforementioned treatment methodology. Prior to treatment, subject B complained of scalp pain and pressure for several years that coincided with gradual hair loss. Subject B reported cessation of scalp pain after receiving only two treatments to her scalp and back. In addition, subject B reports a perceived improvement to the condition of her scalp, in that the skin of her scalp is more pliable, soft, and has more movement. In addition, subject B reports that hair loss is starting to subside, and that the hair feels more manageable to the touch. Subject B also reports anecdotally that loosening of the skin and release of tension in the upper back and face has also resulted in a reduction in wrinkles.

In summary, the present invention teaches of a method for applying a therapeutic signal to a body portion to encourage hair growth. The method employs electrical stimulation and a circular massaging motion that loosens connective tissue thereby improving the nutritional factor of the subject body portion. In addition, the method is performed on successive body portions to achieve subject relaxation, pain relief, and commensurate stress reduction.

Although the preferred embodiments of the invention have been illustrated and described in detail, it will be readily apparent to those skilled in the art that various modifications may be made therein without departing from the spirit of the invention or from the scope of the appended claims.

What is claimed is:

1. A method of applying a therapeutic signal to a body portion of a subject to encourage hair growth, said method comprising:

securing a first electrode in contact with a skin surface of said subject remote from said body portion, said first electrode being maintained at a ground potential from which said therapeutic signal is referred;

positioning a second electrode at said body portion, said second electrode including a conductive pod and a grip interconnected with said conductive pod;

providing said therapeutic signal at said conductive pod; and manipulating said second electrode by an operator at said body portion, said operator utilizing both hands to manipulate said second electrode such that a first one of said hands applies pressure to said conductive pod, a second one of said hands applies force on said grip, and said hands act cooperatively to apply a circular motion to said body portion underlying said conductive pod; and repetitively applying said circular motion as said conductive pod is moved across said body portion to loosen connective tissue at said body portion.

2. A method as claimed in claim 1 further comprising:
utilizing an apparatus that includes a plurality of digital waveform generators, and a combiner in communication with said second electrode; and
said providing operation comprises:
  producing, at said digital waveform generators, different resultant signals related to a reference signal; and
  combining said different resultant signals at said combiner to produce said therapeutic signal for provision to said second electrode.

3. A method as claimed in claim 2 wherein said producing step comprises generating said different resultant signals that are harmonically non-related to form said therapeutic signal.

4. A method as claimed in claim 1 wherein said conductive pod of said second electrode has an arcuate side and a generally flat side, said arcuate side and said flat side being coupled along corresponding longitudinal edges and merging at an end to form an electrode tip, and said positioning operation comprises selectively utilizing one of said arcuate side, said flat side, and said longitudinal edges.

5. A method as claimed in claim 4 further comprising:
selecting said body portion to be a region surrounding the eyes; and
utilizing said electrode tip for said region surrounding the eyes.

6. A method as claimed in claim 1 further comprising selecting said body portion from a group consisting of the shoulders, sides of the head, top of the head, forehead, and surrounding the eyes.

7. A method as claimed in claim 1 further comprising successively performing said positioning, said providing, said manipulating, and said repetitively applying operations at each of the shoulders, the sides of the head, the top of the head, the forehead, and surrounding the eyes.

8. A method of applying a therapeutic signal to a body portion of a subject to encourage hair growth, said method comprising:
securing a first electrode in contact with a skin surface of said subject remote from said body portion, said first electrode being maintained at a ground potential from which said therapeutic signal is referred;
positioning a second electrode at said body portion, said second electrode including a conductive pod, said conductive pod having an arcuate side and a generally flat side, said arcuate side and said flat side being coupled along corresponding longitudinal edges and merging at an end to form an electrode tip, and said positioning operation including selectively utilizing one of said arcuate side, said flat side, and said longitudinal edges;
providing said therapeutic signal at said conductive pod, said providing operation including:
  producing, at a plurality of digital waveform generators in a treatment apparatus, different resultant signals related to a reference signal; and
  combining said different resultant signals to produce said therapeutic signal;

manipulating said second electrode by an operator at said body portion to apply a circular motion to said body portion underlying said conductive pod; and
repetitively applying said circular motion as said conductive pod is moved across said body portion to loosen connective tissue at said body portion.

9. A method as claimed in claim 8 wherein said producing step comprises generating said different resultant signals that are harmonically non-related to form said therapeutic signal.

10. A method as claimed in claim 8 further comprising:
selecting said body portion to be a region surrounding the eyes; and
utilizing said electrode tip for said region surrounding the eyes.

11. A method as claimed in claim 8 further comprising successively performing said positioning, said providing, said manipulating, and said repetitively applying operations at each of the shoulders, the sides of the head, the top of the head, the forehead, and surrounding the eyes.

12. A method of applying a therapeutic signal to a body portion of a subject to encourage hair growth, said method comprising:
selecting said body portion from a group consisting of the shoulders, sides of the head, top of the head, forehead, and surrounding the eyes;
securing a first electrode in contact with a skin surface of said subject remote from said body portion, said first electrode being maintained at a ground potential from which said therapeutic signal is referred;
positioning a second electrode at said body portion, said second electrode including a conductive pod, and said conductive pod having an arcuate side and a generally flat side, said arcuate side and said flat side being coupled along corresponding longitudinal edges and merging at an end to form an electrode tip, and said positioning operation including selectively utilizing one of said arcuate side, said flat side, and said longitudinal edges;
providing said therapeutic signal at said conductive pod;
manipulating said second electrode by an operator at said body portion to apply a circular motion to said body portion underlying said conductive pod; and
repetitively applying said circular motion as said conductive pod is moved across said body portion to loosen connective tissue at said body portion.

13. A method as claimed in claim 12 further comprising:
utilizing an apparatus that includes a plurality of digital waveform generators, and a combiner in communication with said second electrode; and
said providing operation comprises:
  producing, at said digital waveform generators, different resultant signals related to a reference signal; and
  combining said different resultant signals at said combiner to produce said therapeutic signal for provision to said second electrode.

14. A method as claimed in claim 13 wherein said producing operating comprises generating said different resultant signals that are harmonically non-related to form said therapeutic signal.

15. A method as claimed in claim 12 further comprising successively performing said positioning, said providing, said manipulating, and said repetitively applying operations at each of the shoulders, the sides of the head, the top of the head, the forehead, and surrounding the eyes.

* * * * *